United States Patent [19]

Watkins et al.

[11] Patent Number: 5,152,792
[45] Date of Patent: Oct. 6, 1992

[54] APPARATUS AND METHOD FOR GAUGING AND CONTROLLING PROCESS STEPS USED TO REMOVE PROSTHETIC JOINTS

[75] Inventors: F. Thomas Watkins, Menlo Park; Albert K. Chin, Palo Alto, both of Calif.

[73] Assignee: Zimmer, Inc., Warsaw, Ind.

[21] Appl. No.: 475,778

[22] Filed: Feb. 6, 1990

[51] Int. Cl.$^5$ .......................... A61F 2/28; A61F 5/04
[52] U.S. Cl. ....................... 623/16; 606/87; 606/99
[58] Field of Search ............ 623/16, 18, 20, 23; 606/60, 61, 70, 99, 87

[56] References Cited

U.S. PATENT DOCUMENTS

| | | | |
|---|---|---|---|
| 4,222,382 | 9/1980 | Antonsson et al. | 128/92 |
| 4,248,232 | 2/1981 | Engelbrecht et al. | 128/305 |
| 4,399,813 | 8/1983 | Barber | 128/92 |
| 4,463,753 | 8/1984 | Gustilo | 128/92 |
| 4,476,861 | 10/1984 | Dimakos et al. | 128/303 |
| 4,612,922 | 9/1986 | Barber | 128/92 |
| 4,686,971 | 8/1987 | Harris et al. | 128/92 |
| 4,702,236 | 10/1987 | Tarabichy | 128/92 |
| 4,834,081 | 5/1989 | Van Zile | 128/92 |
| 4,838,264 | 6/1989 | Bremer | 128/303 |

OTHER PUBLICATIONS

Synthes "Original Instruments", Wayne, Pa., Aug. 1984, pp. (1)-7, (1)-8; (3)3-10.
"Möglichkeiten der Anwendung von Ultraschallwerkzeug bei Endoprothesenwechsel", E. Nieder, E. Engelbrecht, U. Röder und E. Strickle, Der Chirurg, 1979.
*Techniques in Orthopedics,* "Revision of Total Hip and Knee", Lawrence D. Dorr, M.D., pp. 14-22.
"Revision in Surgery for Failed, Monseptic Total Hip Arthroplasty-The Femoral Side", William H. Harris, M.D., pp. 8-20.

*Primary Examiner*—David Isabella
*Attorney, Agent, or Firm*—Todd A. Dawson

[57] ABSTRACT

Over tightening of the threaded rods used to engage and remove the cement for prosthetic joints is avoided by measuring the depth of the passages into which the rods are threaded and providing sleeves on the rods which serve as visual indicia of the extent of penetration of the rods into the cement. A depth gauge calibrated in both units of length and screw thread turns is provided for the measuring function. The sleeves are slidably received on the rods and proportioned to engage the edges of the passages into which the rods are threaded. In use, the sleeves slide toward a marker as the rods are threaded into place.

7 Claims, 5 Drawing Sheets

APPARATUS AND METHOD FOR GAUGING AND CONTROLLING PROCESS STEPS USED TO REMOVE PROSTHETIC JOINTS

RELATED APPLICATIONS

This application relates to U.S. application Ser. No. 255,650, filed Oct. 11, 1988 now U.S. Pat. No. 4,919,153, and continuation in part U.S. application Ser. No. 467,742, filed Jan. 19, 1990, both of which applications are in the name of Albert K. Chin, one of the co-inventors herein. The present application also relates to and is concerned with an improvement in the invention of application Ser. No. 467,724, filed Jan. 19, 1990 by Milton B. McColl and Albert K. Chin.

BACKGROUND OF THE INVENTION

Related U.S. Pat. No. 4,919,153 is concerned with a method and apparatus for removing the cement mantle used to secure a prosthetic appliance within a bone cavity and, more particularly, is concerned with a technique wherein a new mass of cement is adhered in place within the mantle and a pulling tool is then employed to remove the mass and the mantle as a unit. Application Ser. No. 467,724 and application Ser. No. 467,742 are concerned with improvements wherein the cement mantle and newly injected mass of cement are removed in increments to avoid the severe stresses which are sometimes encountered in removing the cement mantle and newly injected mass of cement as a single unit. Application Ser. No. 467,724 is particularly concerned with an improvement of the latter type wherein a plurality of pulling tools of different lengths are successively screwed into the newly injected mass of cement to affect the incremental removal of the mantle.

The apparatus and method of application Ser. No. 467,724 functions well, except for the possibility of stripping out the threads formed in the cement mass into which the pulling tools are threaded. The enlarged diameter shoulders on the pulling tools of the latter application are designed to give the surgeon tactile indication that the pulling tool has been threaded into the cement plug completely. In practice, however, it is difficult for the surgeon to feel the difference between a pulling tool that is fully threaded into the cement plug, and one that has been overtightened. A T-handled wrench is used to thread the extraction rod into place, and substantial torque can be developed during placement. Overtightening of the extraction rod can cause the threads formed in the new cement to strip out, thus rendering the system useless.

One method of dealing with the thread stripping problem encountered in using the pulling tools of application Ser. No. 467,724 is to count the number of turns corresponding to the desired depth of pulling tool insertion. While this method works, it is slow and cumbersome. It also requires that the number of turns be calculated in advance and carefully counted as the tool is threaded into place.

SUMMARY OF THE INVENTION

The present invention employs a sleeve telescopically received on the pulling tool. The sleeve has an inner diameter providing a sliding fit with the tool and an outer diameter small enough to allow it to pass down the femoral canal. An indicator or stop ring is provided on the pulling tool to the proximal end of the sleeve. In use, the sleeve is initially disposed so as to expose only a limited number of threads at the distal portion of the tool. The tool is introduced into the threaded plug of new cement and threaded into place in the same manner as in the method of application Ser. No. 467,724. As the tool is threaded into the plug, the sleeve is displaced proximally toward the indicator or stop ring. When the sleeve reaches the indicator or ring, the surgeon knows that the tool has been threaded into place to the proper depth.

The present invention also provides a gauge to measure the depth of the screw-threaded passage formed in the plug of cement. The gauge enables the surgeon to determine how many successive tools will be required to affect the incremental removal of the entire plug. The gauge also provides means to measure the number of turns to which the last of the successive tools may be turned into place. This number is generally less than the total number of turns for which the tool is designed, since the last segment of the plug is rarely the exact length of the threads provided on the pulling tool.

The gauge takes the form of an elongate rod having a diameter less than that of the threaded passage being measured A tube having a diameter greater than that of the passage is slidably disposed around the rod. Indicia on the rod indicate the longitudinal position of the tube relative to the rod.

A principal object of the invention is to provide an improved method and apparatus to control the extent to which pulling tools are threaded into a cement plug being used to remove the cement mantle for a prosthetic joint.

Another and more specific object of the invention is to provide such a method and apparatus which avoids overtightening of the pulling tool and stripping of the threads within the plug.

Yet another object of the invention is to provide a gauge for measuring the depth of the threaded passage within the plug so that the number of pulling tools required to fully remove the plug can be determined.

Still another object of the invention is to provide such a gauge with which to measure the maximum number of turns to which a pulling tool may be threaded into place within the plug.

A further and more general object of the invention is to provide a simplified and essentially foolproof method and apparatus for avoiding overtightening the pulling tools used for incrementally removing a cement mantle from a bone cavity.

These and other objects will become more apparent when viewed in light of the following detailed description and accompanying drawings.

BRIEF DESCRIPTION OF THE DRAWINGS

FIG. 19 is a cross-sectional elevational view similar to FIG. 18, illustrating the fourth of the successive pulling tools at the termination of being threaded into the passage within the remaining plug of cement; and, FIG. 20 is a cross-sectional elevational view similar to FIG. 19, illustrating the fourth pulling tool coupled to a slap hammer and in the process of breaking away and removing the final segment of the plug of cement.

DESCRIPTION OF THE PREFERRED EMBODIMENTS

Figures 1, 2, 3, 4:
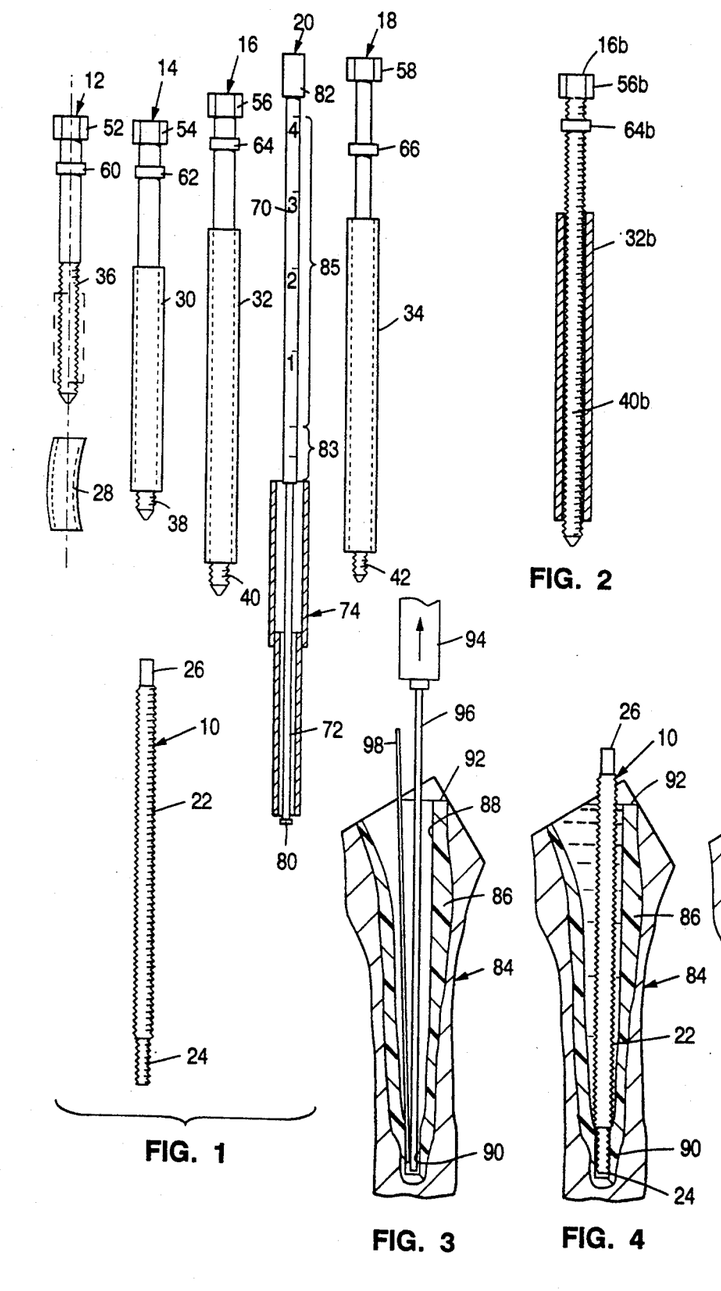
FIG. 1 is an elevational view, with parts thereof shown in section, of the kit of basic elements used to practice the invention, including the thread forming die, four successive pulling tools, and the gauge.
FIG. 2 is a cross-sectional elevational view of a modified form of a pulling tool which may be used in the practice of the invention.
FIG. 3 is a cross-sectional elevational view of the upper femur of a leg, wherein the femoral component of a prosthetic hip joint has been removed from a cement mantle within the femur and a new mass of cement is in the process of being injected into the cavity left in the mantle by removal of the component.
FIG. 4 is a cross-sectional elevational view similar to FIG. 3, illustrating the step of using a thread forming die to form a threaded passage within the mass of new cement injected into the mantle.

The kit shown in FIG. 1 includes the following components: thread forming die 10, first successive pulling tool 12, second successive pulling tool 14, third successive pulling tool 16, fourth successive pulling tool 18, and depth gauge 20. The die 10 is of the same construction as that of U.S. patent application Ser. No. 467,724 and includes a main portion 22 of a uniform enlarged cross-section and a distal end portion 24 of a reduced cross-section, as compared to that of the main portion. Both the main portion 22 and the distal portion 20 are threaded over their lengths with continuous screw threads of the same pitch (e.g. machine screw pitch 20). The top end of the die is provided with a square 26 whereby the die may be turned with a wrench. The die may be formed of a metal or a polymer and ideally is provided with a non-stick external surface over the threaded portions. The non-stick surface may be a permanent integral part of the die, such as TEFLON, and/or a release coating, such as DOW CORNING 20 of the Dow Corning Corporation of Midland, Mich.

The pulling tools 12, 14, 16 and 18 are each of a bolt-like construction and fabricated of steel rod, with a polymer sleeve telescopically received thereon. The sleeves for the tools 12, 14, 16 and 18 are designated, respectively, by the numerals 28, 30, 32 and 34. In a typical embodiment, the tool 12 has a length of four inches, the tool 14 six inches, the tool 16 eight inches and the tool 18 nine inches. Each tool terminates in a conical distal end and has a distal portion adjacent said end formed with external machine screw threads. The threaded sections formed on the tools 12, 14 and 16 are designated by the numerals 36, 38 and 40, respectively, and have a length of approximately 1½ inches and an o.d. of ¼ inch. The threaded section of the tool 18 has a length of approximately ¾ of an inch and an o.d. of ⅛ inch. The screw threads on the pulling tools are complemental with the threads formed by the die 10.

The tools 12, 14, 16 and 18 are formed with unthreaded sections 44, 46, 48 and 50, respectively, above the threaded sections thereof. Enlarged hexagonal heads 52, 54, 56 and 58, respectively, are formed on the proximal ends of the tools 12, 14, 16 and 18. The heads provide means whereby torsional and pulling forces may be applied to the tools.

Stop collars 60, 62, 64 and 66 are fixed, respectively, to the tools 12, 14, 16 and 18. The collars serve as markers and abutments for the sleeves 28, 30, 32 and 34. The sleeves are proportioned to frictionally engage the pulling tools to an extent sufficient to resist inadvertent sliding movement relative thereto, while permitting such movement in response to external forces applied to the sleeves as they are threaded into a plug of cement. This proportioning may be provided by cutting the sleeves from an arcuate length of tubing, whereby each sleeve has an arcuate shape (see the sleeve 28 in FIG. 1) which is straightened as the sleeve is telescoped onto a pulling tool. Alternatively, it might be provided by forming the sleeves of tubing having an internal diameter slightly less than the external diameter of the threaded sections of the tools and slitting the sleeves longitudinally to permit their expansion. The lengths of the sleeves 28, 30, 32 and 34 are chosen so that, when engaged with the stop collars, the sleeves will cover only the most proximal screw threads of the tools. As a result of the latter dimensional interrelationship, a surgeon using one of the tools will visually observe the sleeve on the tool approaching the stop collar as the tool is threaded into place. When the sleeve contacts the stop collar, the surgeon will know that the tool is fully threaded into place and that no additional torsional forces should be applied to the tool. It will be appreciated that when fully threaded into place, the sleeves on the tools function to shield the most proximal threads of the tools against being threaded into place in the cement being engaged. Thus, the tool cannot be threaded against the shoulder provided by the unthreaded portion thereof.

FIG. 2 shows a modified pulling tool which corresponds to the tool 16, except that the shaft of the tool is threaded over its full length, rather than a limited distal portion. The elements of the tool shown in FIG. 2 are designated by numerals corresponding to those used for the tool 16, followed by the subscript "b", as follows: tool $16_b$; sleeve $32_b$; threaded section $40_b$; hexagonal head $56_b$; and stop collar $64_b$. In use, the tool $16_b$ operates in the same manner as the aforedescribed tools. Although the full length of the shaft of the tool $16_b$ is externally threaded, the sleeve $32_b$ serves to shield the threads on all but the distal portion of the shaft. The tool $16_b$ has the advantage that it may be fabricated of fully threaded rod stock, without the necessity of providing an unthreaded section on the tool shaft.

The gauge 20 is provided to measure the depth of the screw threaded passage formed by the die 10. The elements of the gauge comprise: an indicator rod 68 having an enlarged diameter proximal portion 70 and a reduced diameter distal portion 72; a tube 74 telescopically received on the rod 68, said tube having an enlarged segment proportioned for slidable receipt of the proximal portion 70 and a reduced diameter segment 78 proportioned for slidable receipt of the distal portion 72; an enlarged tip 80 fixed to the end of the distal portion 72; and, an enlarged handle 82 fixed to the proximal portion 70. The external surface of the proximal portion 70 is provided with indicia to indicate the longitudinal position of the rod 68 relative to the tube 74. The indicia at the lower end of the proximal portion 70 are designated by the numeral 83 and calibrated to measure screw thread turns. The indicia on the upper length of the proximal portion 70 are designated by the numeral 85 and calibrated to measure the number of pulling tools required to fully remove the mantle of cement being worked upon.

DESCRIPTION OF THE METHOD STEPS

The use of the apparatus in carrying out the method steps is depicted sequentially in FIGS. 3 to 20. As there shown, the femur being worked upon is designated in its entirety by the numeral 84 and is illustrating after the femoral component of a prosthetic hip joint has been removed therefrom for replacement. These figures also show that the trochanter of the femur has been removed to facilitate the method.

FIG. 3 shows the femur 84 after the femoral component of the hip joint has been removed, with the cement mantle 86 which is to be removed left in place within the bone recess within the femur. As there shown, the cavity 88 within the mantle has been cleaned and a reduced diameter extension, designated 90, has been drilled into the distal end of the mantle. The top of the mantle has also been cut to provide a horizontal surface, as designated by the numeral 92.

The first step of preparing the mantle for removal comprises injecting cement into the cavity 88. This step is illustrated in FIG. 3 wherein an injection gun 94 is shown injecting cement to the bottom of the cavity through a thin snout 96. A vent tube 98 is extended to the bottom of the cavity to assure that air will be vented therefrom and that the cavity will be filled to the bottom. As the cavity is filled with cement, the gun and snout are slowly retracted, as depicted by the arrow line in FIG. 3. The vent tube 98 would be withdrawn after the reduced diameter extension 90 is adequately filled. Most typically, the mantle 86 is comprised of old methylmethacrylate cement. This type of cement is capable of being partially dissolved and softened by the application of new like fluid cement thereto. Accordingly, assuming that the mantle is comprised of such cement, the new cement injected into the cavity 88 would be a like cement and, ultimately, bond to the original mantle and form an integral part thereof.

FIG. 4 shows the mantle filled with new cement to the level of the horizontal surface 92 and the step of forming a screw threaded passage through the plug of new cement. As there shown, the die 10 has been screwed to essentially the bottom of the cavity to form a screw threaded passage therein. It should also be appreciated that the die is provided with a non-stick coating prior to being so screwed into place, either in the form of an integral surface formed as part of the die and/or a non-stick coating applied to the die.

Figure 5:
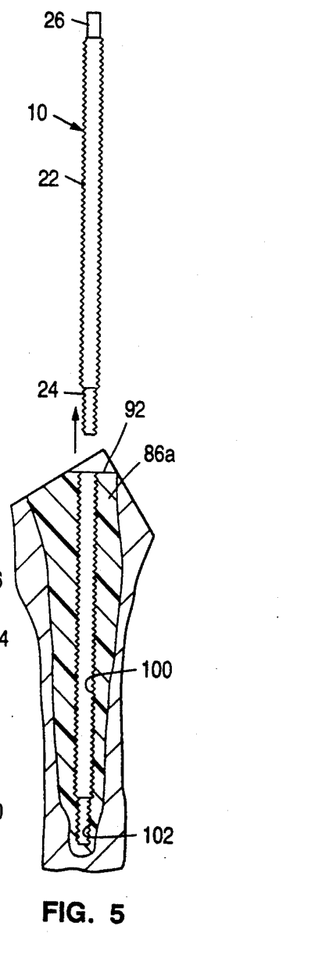
FIG. 5 is a cross-sectional elevational view similar to FIG. 4, illustrating removal of the thread forming die from the mass of new cement to leave a threaded passage therein.

FIG. 5 shows the mantle, now in the form of a unitary plug $86_a$, after the newly injected cement has cured and formed an integral mass with the mantle. As shown in FIG. 5, the die 10 has been threaded out of the plug, leaving a passage comprised of an enlarged proximal portion 100 and a reduced diameter distal portion 102.

Figures 6, 7:
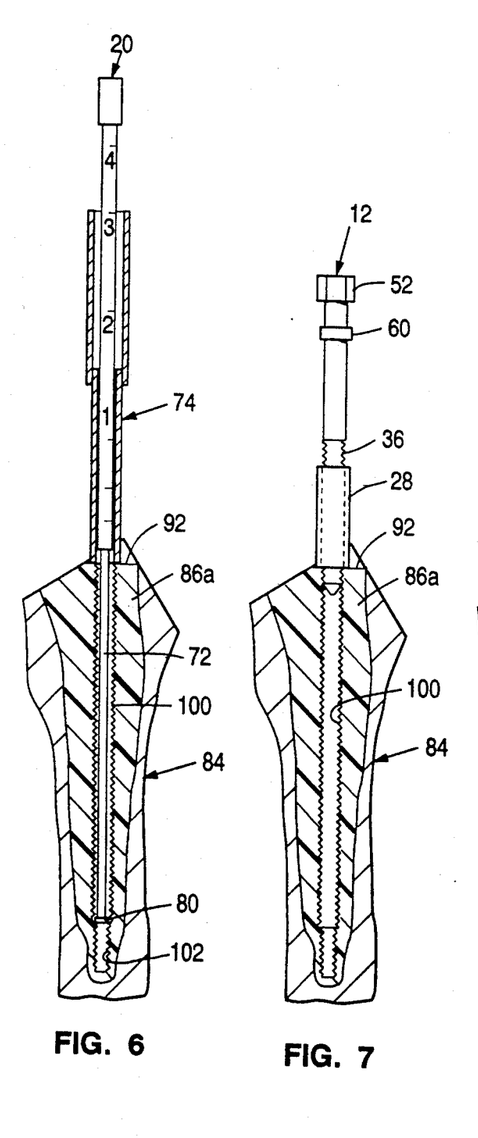
FIG. 6 is cross-sectional elevational view similar to FIG. 5, illustrating the use of the gauge of the present invention to measure the depth of the threaded passage in the mass of new cement.
FIG. 7 is a cross-sectional elevational view similar to FIG. 6, illustrating the first of the successive pulling tools at the commencement of being threaded into the passage within the plug comprised of the mass of new cement and the cement of the old mantle.

FIG. 6 shows the gauge 20 in the process of measuring the depth of the passage within the plug $86_a$. As there shown, it will be seen that the rod 68 is extended to the bottom of the proximal portion 100 of the passage. This figure also illustrates that the rod has a diameter less than the internal diameter of the passage and that the tip 80 has a cross-section less than the portion 100 and greater than the portion 102. As a result of the latter characteristic, the tip engages the shoulder between the portions 100 and 102 and the depth being measured by the gauge is actually that of only the portion 100. From FIG. 6, it will be seen that the upper edge of the tube 74 registers with a portion of the indicia 85 between the numerals 3 and 4 indicating the number of tools which will be required to remove the mantle. This means that four tools will be required for the process and that the third tool will need to be threaded into less than the full length of the threaded section on the tool.

Figure 8:
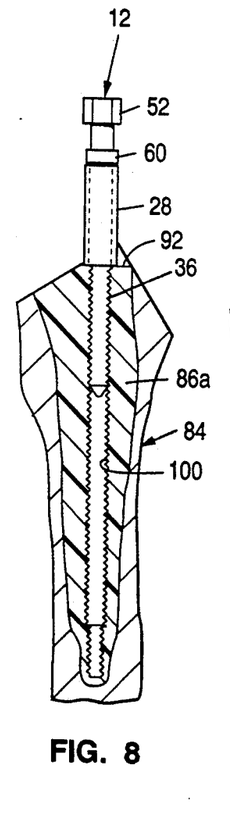
FIG. 8 is a cross-sectional elevational view similar to FIG. 7, illustrating the first of the successive pulling tools at the termination of being threaded into the passage within the plug.

FIGS. 7 and 8 show the first tool 12 in the process of being threaded into place in the mantle plug $86_a$. As shown in FIG. 7, the distal threads only of the tool are engaged and the sleeve 28 is engaged with the surface 92. FIG. 8 shows the tool 12 threadably engaged with the proximal portion 100 of the passage to the maximum extent desired, as indicated by contact of the sleeve 28 with the stop 60. It will be appreciated that in the process of being threaded from the condition shown in FIG. 7 to that shown in FIG. 8, the surgeon would visually observe the sleeve 28 sliding toward the stop 60 and stop the threading process when the pulling tool reaches the point shown in FIG. 8.

Figure 9:
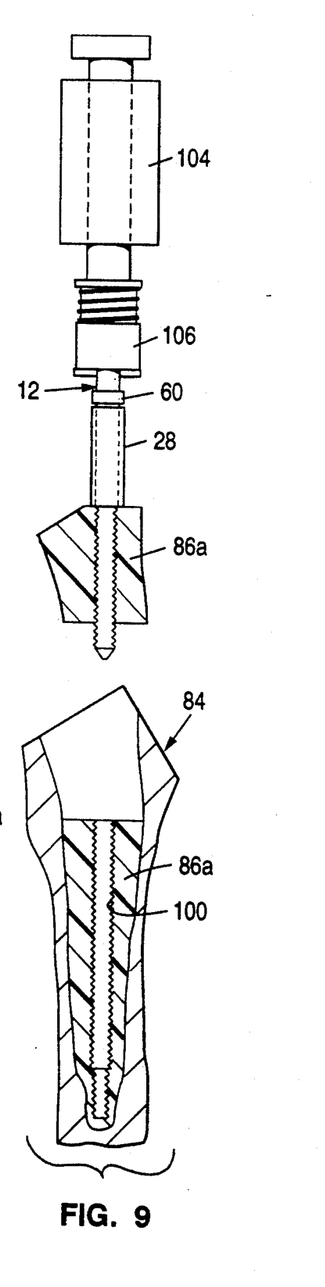
FIG. 9 is a cross-sectional elevational view similar to FIG. 8, illustrating a slap hammer coupled to the first pulling tool and in the process of breaking away and removing a segment of the plug.
Figure 10:
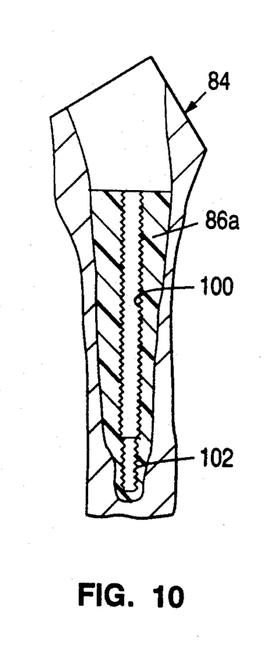
FIG. 10 is a cross-sectional elevational view similar to FIG. 9, illustrating the plug of cement which remains after the step of FIG. 9.

FIG. 9 shows the tool 12 connected to a slap hammer 104 through a coupling 106. As there shown, pulling force has been applied to the upper portion of the mantle plug 86$_a$ and that portion or segment, designated 86$_{a1}$ has been removed from the femur 84. Such removal is possible because a methylmethacrylate cement has very little tensile strength and readily fractures upon being subjected to tensile force by the slap hammer.

Figure 11:
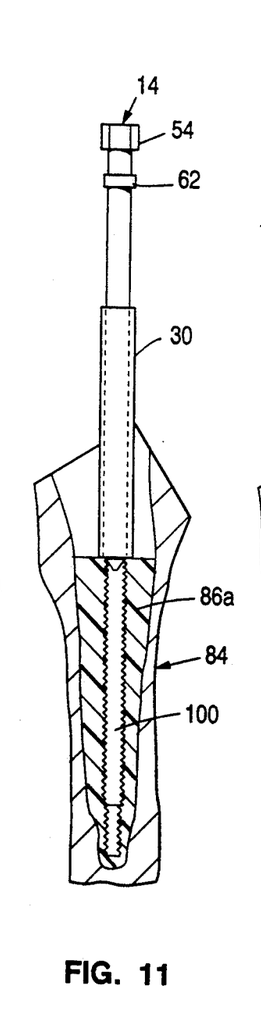
FIG. 11 is a cross-sectional elevational view similar to FIG. 10, illustrating the second of the successive pulling tools at the commencement of being threaded into the passage within the remaining plug of cement.
Figures 12, 13:
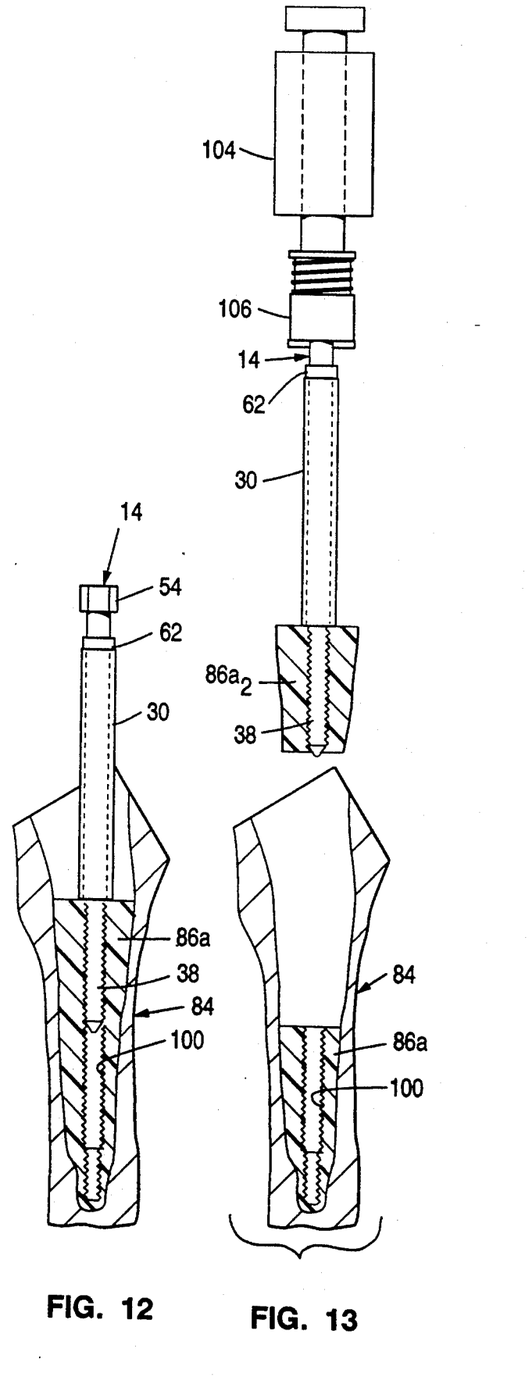
FIG. 12 is a cross-sectional elevational view similar to FIG. 11, illustrating the second of the successive pulling tools at the termination of being threaded into the passage within the remaining plug of cement.
FIG. 13 is a cross-sectional elevational view similar to FIG. 12, illustrating a slap hammer connected to the second pulling tool and in the process of breaking away and removing a second segment of the plug of cement.

FIGS. 11 and 12 show the second pulling tool 14 in the process of being threaded into place in the mantle plug 86$_a$ in essentially the same manner that the first pulling tool is depicted as being threaded into place in FIG. 7 and 8. In FIG. 11, the threading process is at its commencement, with the sleeve 30 against the top surface of the mantle plug. FIG. 12 shows the tool 14 threaded into the mantle plug to the full extent desired, as indicated by abutment of the sleeve 30 with the stop 62.

FIG. 13 shows the slap hammer 104 connected to the tool 14 and the segment 86$_{a2}$ as having been removed from the femur by the operation of the slap hammer. Again, it should be appreciated that the low tensile strength of the methylmethacrylate cement enables the segment 86$_{a2}$ to be fractured away from the portion of the mantle plug remaining in the femur.

Figure 14:
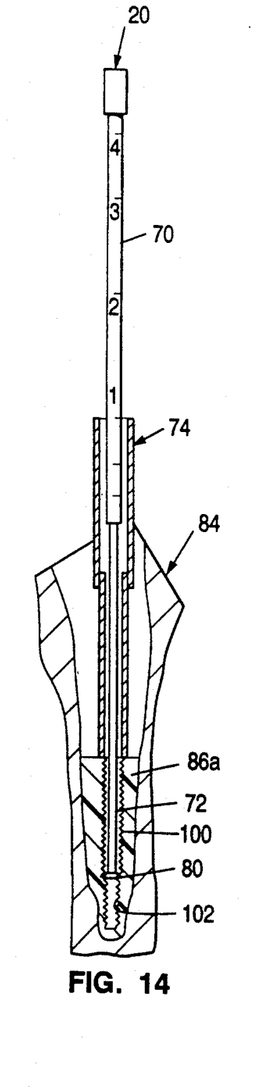
FIG. 14 is a cross-sectional elevational view similar to FIG. 13, illustrating the gauge in the process of measuring the depth of the threaded passage in the plug of cement remaining after the step of FIG. 13.

FIG. 14 shows the gauge 20 in the process of measuring the length of the proximal passage portion 100 remaining after removal of the segment 86$_{a2}$. From this figure, it will be seen that the upper end of the tube 74 registers with the screw thread measuring indicia 83 on the rod 68. This results because the depth of the threads being measured is less than the maximum exposed threads on a pulling tool when the sleeve on the tool is against the stop collar. The resulting measurement on the rod indicates the number of turns required to thread a pulling tool to the bottom of the threaded proximal portion 100, without overtightening.

Figure 15:
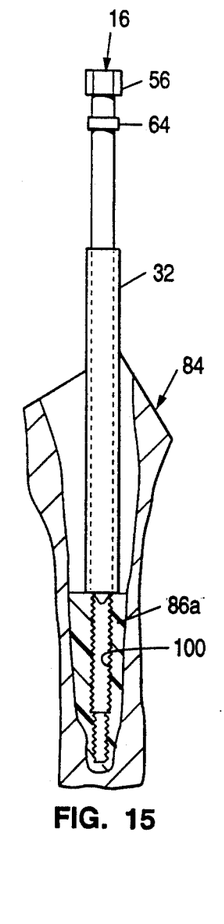
FIG. 15 is a cross-sectional elevational view similar to FIG. 14, illustrating the third of the successive pulling tools at the commencement of being threaded into the passage within the remaining plug of cement.
Figures 16, 17:
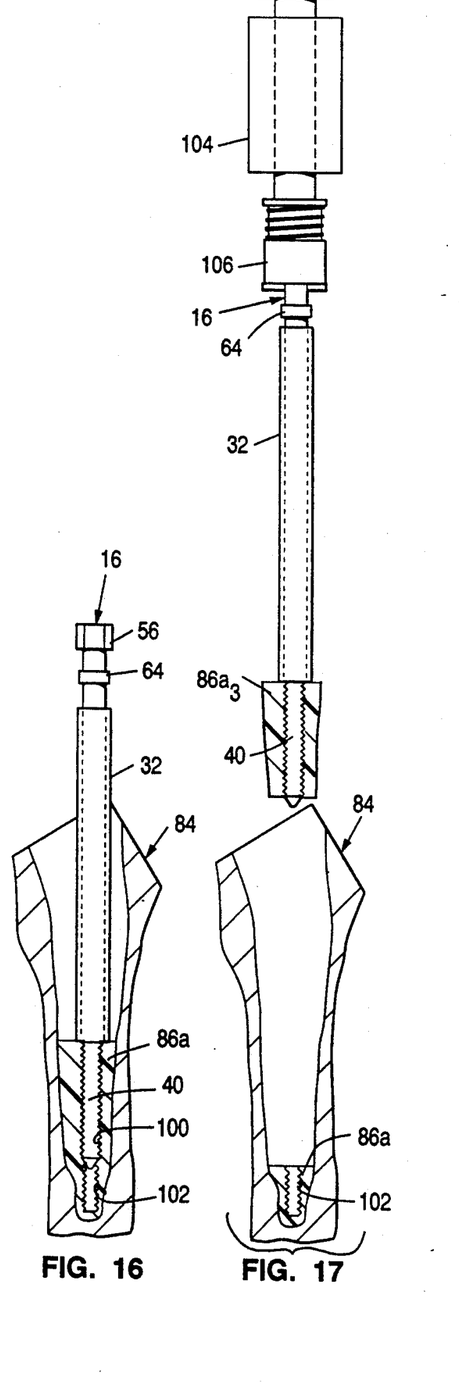
FIG. 16 is a cross-sectional elevational view similar to FIG. 15, illustrating the third of the successive pulling tools at the termination of being threaded into the passage within the remaining plug of cement.
FIG. 17 is a cross-sectional elevational view similar to FIG. 16, illustrating a slap hammer coupled to the third pulling tool and in the process of breaking away and removing a segment of the plug of cement.

FIGS. 15 and 16 illustrate the third pulling tool 16 in the process of being threaded into the remaining cement mantle plug 86$_a$. As shown in FIG. 15, the threading process is at the commencement stage and the sleeve 32 is against the top of the plug. FIG. 16 shows the tool threaded into the plug to the maximum extent and illustrates that the sleeve 32 has not abutted the stop collar 64. The latter condition results because the tool has been threaded into place by the number of turns indicated by the gauge in the step depicted in FIG. 14; and this number of turns results in less than full extension of the threaded section 40 from the sleeve 32.

FIG. 17 shows the slap hammer 104 connected to the tool 16 and a segment 86$_{a3}$ as having been removed from the femur by operation of the slap hammer. As there shown, it will be seen that only the distal portion of the mantle plug remains within the femur.

Figure 18:
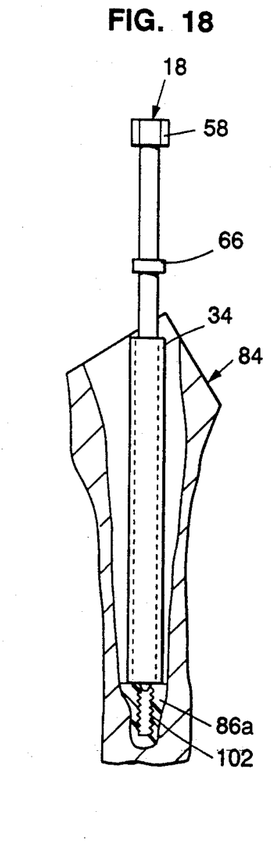
FIG. 18 is a cross-sectional elevational view similar to FIG. 17, illustrating the fourth of the successive pulling tools at the commencement of being threaded into the passage within the remaining plug of cement.
Figures 19, 20:
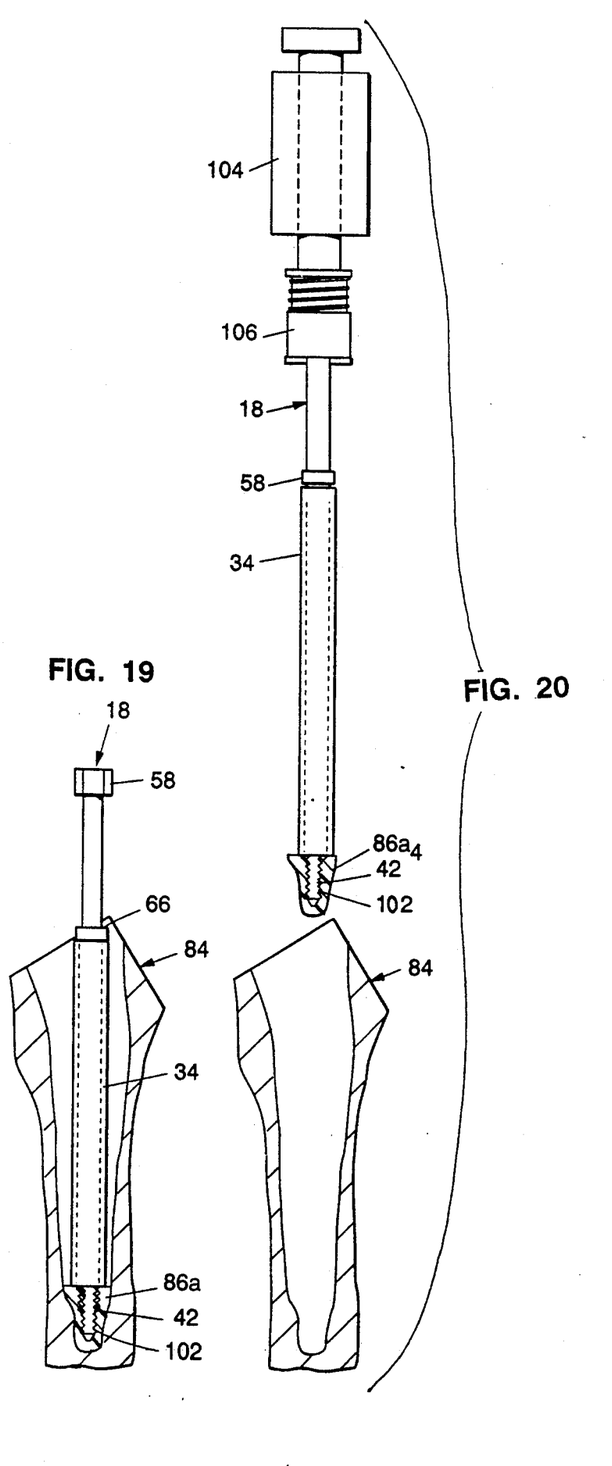

FIGS. 18 and 19 depict the step of threading the fourth tool 18 into the final reduced diameter segment of the mantle. As shown in FIG. 18, the process of threading the tool into the mantle segment is at its commencement. FIG. 19 shows the tool fully threaded into place, as is apparent from contact of the sleeve 34 with the stop 66. It will be appreciated that during the process moving from the condition shown in FIG. 18 to that of FIG. 19, the surgeon visually observes the sleeve 34 moving toward the stop collar 66 and exercises care not to tighten the tool beyond the point where the sleeve contacts the collar.

FIG. 20 shows the final step of removing the mantle segment 86$_{a4}$ from the femoral cavity. As there shown, the slap hammer 104 is connected to the tool 18 and the plug segment 86$_{a4}$ has been removed by operation of the slap hammer.

CONCLUSION

From the foregoing description, it should be apparent that the present invention provides an apparatus and method to avoid the overtightening of the tools used for the incremental removal of cement mantles for prosthetic joints. At the same time, the invention provides a means whereby the surgeon may be fully informed in advance of the length of the mantle being removed and the number of steps which will be required for its removal.

While preferred embodiments of the invention have been illustrated and described, it should be understood that the invention is not intended to be limited to the specifics of these embodiments, but rather is defined by the accompanying claims.

What is claimed is:

1. A kit for removing a mantle of cement having an elongate cavity formed therein from adhered condition within a bone recess, said kit comprising;
    (a) a die for forming an elongate screw threaded passage within a mass of cement injected into the cavity;
    (b) a first elongate pulling element of a predetermined length, said element having a screw threaded section complemental with a screw threaded passage formed by the die;
    (c) a second elongate pulling element of a predetermined length, said second element having a screw threaded section complemental with a screw threaded passaged formed by the die;
    (d) torque transmitting means on said first and second elements to enable said elements to be screwed into threaded engagement with a threaded passage formed in a mass of cement by the die;
    (e) indicator means operatively associated with the screw threaded section of the first element to indicate when the extent of the threaded engagement of said section with the passage has reached a predetermined limited extent and enable the extent of such threaded engagement to be controlled to prevent overtightening of said element in the passage;
    (f) grippable means on said first and second elements to enable pulling forces to be applied thereto to remove a mass of cement threadably engaged by the screw threaded sections of the elements from a bone recess; and,
    (g) a gauge for measuring the length of the screw threaded passage comprising an elongated rod having a diameter less than that of the screw threaded passage and a length greater than that of said passage, a tube slidably disposed around the rod having a distal portion of a cross-section greater than the diameter of the threaded passage; and
    (h) indicia means operatively associated with the rod and tube to indicate the longitudinal position of the tube relative to the rod.

2. A kit according to claim 1 wherein said indicia means are calibrated to measure given units of length.

3. A kit according to claim 1 wherein indicia means are calibrated to measure the number of turns of screw threads within the passage.

4. A kit according to claim 1 wherein:

(a) the first and second elongate elements comprise cylindrical shafts, each of which shafts has a predetermined length;

(b) the screw threaded sections of said elements take the form of machine screw threads formed on said shafts; and, (c) the indicator means comprise:
  (1) a sleeve slidably received on the shaft of the first element and having a length less than the length of said shaft; and,
  (2) a marker on the shaft of the first element to enable a comparison of the position of the sleeve relative to said shaft to be made.

5. A kit according to claim 4 further comprising means operatively associating the sleeve and the elongate element to frictionally resist relative movement therebetween, while permitting such movement in response to external forces exceeding a predetermined threshold amount.

6. A kit according to claim 4 wherein the marker comprises a collar fixed to shaft for abutment with the sleeve.

7. A kit according to claim 4 wherein:
(a) the screw threads on the shafts have a base diameter less than the diameter of said shafts;
(b) the screw threads on the first shaft terminate intermediate the length of said shaft so as to leave an unthreaded portion of the shaft; and,
(c) the sleeve is of a length at least equal to the length of the unthreaded portion of the first shaft between the threaded portion of said shaft and the marker.

* * * * *